(12) United States Patent
Zanon et al.

(10) Patent No.: US 8,912,360 B2
(45) Date of Patent: Dec. 16, 2014

(54) METHODS FOR PREPARING RITODRINE HYDROCHLORIDE

(75) Inventors: Jacopo Zanon, Venezia (IT); Giovanna Libralon, Lugano (CH); Carla De Faveri, Treviso (IT); Florian Anton Martin Huber, Dolo (IT)

(73) Assignee: Lundbeck Pharmaceuticals Italy S.p.A., Padua (IT)

( * ) Notice: Subject to any disclaimer, the term of this patent is extended or adjusted under 35 U.S.C. 154(b) by 2 days.

(21) Appl. No.: 13/643,101

(22) PCT Filed: Mar. 24, 2011

(86) PCT No.: PCT/EP2011/054565
§ 371 (c)(1),
(2), (4) Date: Dec. 21, 2012

(87) PCT Pub. No.: WO2011/134724
PCT Pub. Date: Nov. 3, 2011

(65) Prior Publication Data
US 2013/0123539 A1     May 16, 2013

(30) Foreign Application Priority Data
Apr. 29, 2010 (IT) .............................. MI2010A0740

(51) Int. Cl.
*C07C 213/00* (2006.01)
*C07C 209/00* (2006.01)
*C07C 217/00* (2006.01)
*C07C 215/60* (2006.01)
*C07C 213/08* (2006.01)
*C07C 213/10* (2006.01)

(52) U.S. Cl.
CPC ............. *C07C 215/60* (2013.01); *C07C 213/08* (2013.01); *C07C 213/10* (2013.01)
USPC ......................................................... 564/357

(58) Field of Classification Search
None
See application file for complete search history.

(56) References Cited

U.S. PATENT DOCUMENTS

| 3,410,944 | A | 11/1968 | Classen et al. |
| 5,189,219 | A | 2/1993 | Brussee et al. |
| 5,449,694 | A | 9/1995 | Yamazaki et al. |
| 7,408,084 | B2 * | 8/2008 | Nishiyama et al. ........... 564/336 |

OTHER PUBLICATIONS

J. Van Dijk and H.D.Moed, Synthesis of β-phenylethylarnine derivatives X1*N-(Hydroxy—and Methoxy—Aralkyl) derivatives, Recueil des travaux chimiques des pays-bas, Jan. 1, 1973, pp. 1281-1297, vol. 92, No. 12, Elsevier Science Publishers, Amsterdam.
A.D. Sill, C.L. Housmyer and K.Gibboney, Intermediates in the Epimerization of Ritodrine by acid, Tetrahedron, Feb. 11, 1987, pp. 1177-1182, vol. 43, No. 6, Pergamon Journals Ltd, DOI: 10.1016/S0040-4020(01)90058-4.

* cited by examiner

*Primary Examiner* — Clinton Brooks
(74) *Attorney, Agent, or Firm* — Robert E. Alderson Jr.

(57) ABSTRACT

Methods for preparing Ritodrine hydrochloride are provided. Also provided is non-hygroscopic, crystalline, polymorphic Ritodrine hydrochloride of Form I.

6 Claims, No Drawings

METHODS FOR PREPARING RITODRINE HYDROCHLORIDE

CROSS-REFERENCE TO RELATED APPLICATIONS

This application is a National Phase Application of PCT International Application No. PCT/EP2011/054565, International Filing Date, Mar. 24, 2011, claiming priority to Italian Patent Application No. MI2010A000740, filed Apr. 29, 2010, both of which are hereby incorporated by reference in their entirety.

FIELD OF THE INVENTION

A new method for preparing Ritodrine hydrochloride is object of the present invention. The invention also concerns a crystalline polymorphic Ritodrine hydrochloride, Form I, having new and distinctive chemical-physical characteristics. Moreover, Ritodrine hydrochloride solvate or monohydrate or Form II are described, from which it has surprisingly been seen that it is possible to obtain Ritodrine hydrochloride Form I.

BACKGROUND OF THE INVENTION

Ritodrine hydrochloride is a pharmaceutical active ingredient classified as beta2-adrenergic agonist, used for its tocolytic action.

The chemical name of Ritodrine hydrochloride of formula (A) is 4-((1RS,2SR)-1-hydroxy-2-{[2-(4-hydroxyphenyl)ethyl]amino}propyl)phenol hydrochloride.

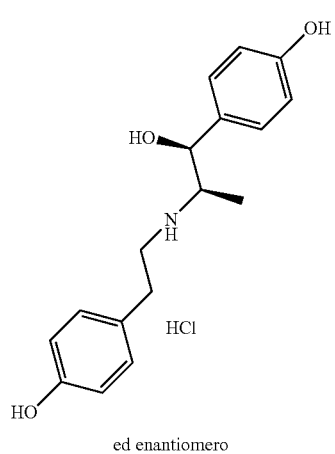

A ed enantiomero

Legenda=and Enantiomer

Ritodrine hydrochloride is the racemate of the erythro form. Ritodrine hydrochloride and its synthesis are described in U.S. Pat. No. 3,410,944. In the examples shown in U.S. Pat. No. 3,410,944, Ritodrine hydrochloride is isolated as a solid having a melting point of 183-186° C. and 193-195° C. Such different melting points are not compatible with a single polymorphic Ritodrine hydrochloride. The crystalline form of a pharmaceutical active ingredient has an impact on its stability, hygroscopicity, solubility, its dissolution speed and its bioavailability. It is therefore fundamentally important to precisely control the crystalline form of the active ingredient and of the methods to obtain it.

A different Ritodrine hydrochloride synthesis process is described in EP0492719 and comprises a non-diastereoselective reduction step with sodium borohydride (NaBH4) that provides an erythro/threo mixture 7.5:1, thus obtaining about 12% of undesired isomer mixture.

EP0603414 describes a stereoselective synthesis for obtaining (−)-Ritodrine hydrochloride and, alternatively, the isolation of (−)-Ritodrine through separation on a chiral column. EP0603414 does not refer to polymorphic forms of the compound.

SUMMARY OF THE INVENTION

The purpose of the present invention is that of providing Ritodrine hydrochloride in a crystalline form that is well defined and stable, hereafter called Form I. Moreover, a further purpose of the present invention is to provide the methods for obtaining such a form.

Ritodrine hydrochloride Form I can be obtained according to the following methods:
(i) treating Ritodrine hydrochloride in alcoholic solvent with one or more organic solvents and subsequent precipitation of Ritodrine hydrochloride Form I;
(ii) transforming Ritodrine hydrochloride solvate or monohydrate or Form II, by suspension in organic solvents, and the subsequent separation of Ritodrine hydrochloride Form I;

or
(iii) transforming Ritodrine hydrochloride solvate or monohydrate or Form II by drying to obtain Ritodrine hydrochloride Form I.

Ritodrine hydrochloride Form I is advantageous since it is stable and it is non-hygroscopic.

Another purpose of the invention is to obtain Ritodrine hydrochloride through a new synthesis process that provides Ritodrine hydrochloride with high yield and purity.

Such a preparation method of Ritodrine hydrochloride foresees:
(a) the reaction of 4-(2-bromopropionyl)phenyl methanesulfonate with benzyl-[2-(4-benzyloxyphenyl)-ethyl]-amine to obtain 4-(2-{benzyl-[2-(4-benzyloxy-phenyl)-ethyl]-amino}-propionyl)-phenyl methanesulfonate (B).
(b) the hydrolysis of the product obtained in (a) in the corresponding deprotected form 2-{Benzyl-[2-(4-benzyloxyphenyl)-ethyl]-amino}-1-(4-hydroxy-phenyl)-propan-1-one (C).
(c) the salification of 2-{Benzyl-[2-(4-benzyloxyphenyl)-ethyl]-amino}-1-(4-hydroxy-phenyl)-propan-1-one (C).
(d) the catalytic hydrogenation of 2-{Benzyl-[2-(4-benzyloxyphenyl)-ethyl]-amino}-1-(4-hydroxy-phenyl)-propan-1-one hydrochloride (D) so as to obtain Ritodrine hydrochloride (A).

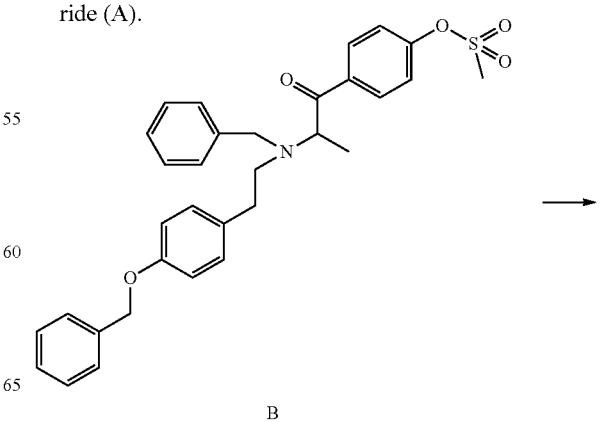

B

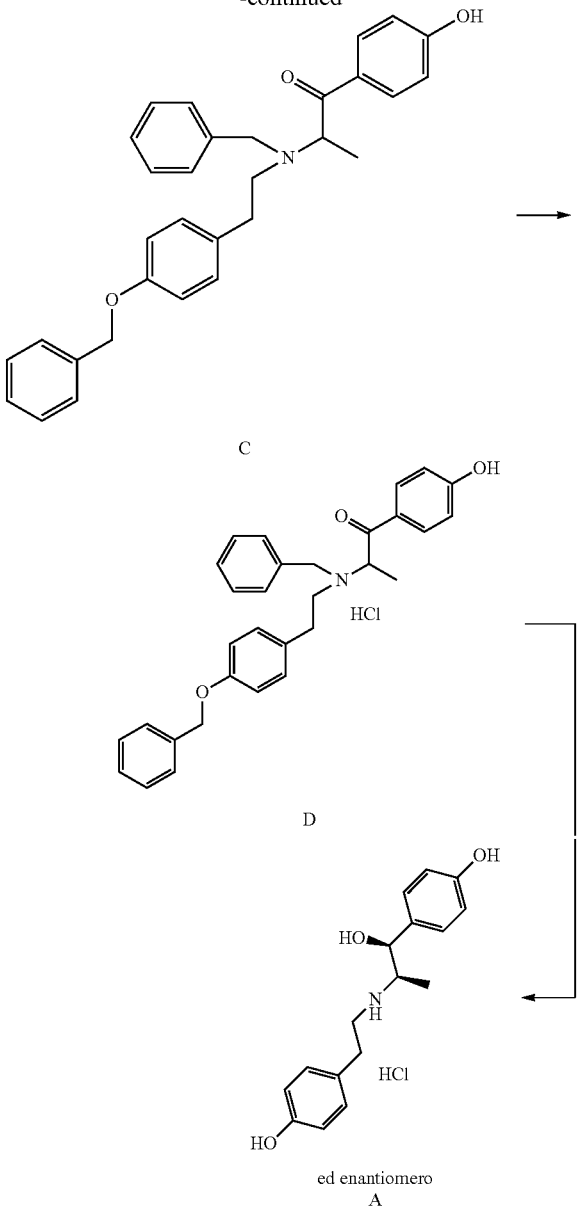

Legenda=and Enantiomer

Further characteristics and advantages of the method according to the invention shall become clearer from the following description and from the preferred embodiments, given as an example and not for limiting purposes.

A more complete understanding of the present invention can be obtained by referring to the tables summarising some chemical-physical characteristics for the compounds named in the rest of the description.

Ritodrine hydrochloride, Form I, Ritodrine hydrochloride, Form II, Ritodrine hydrochloride solvated with acetone, Ritodrine hydrochloride solvated with ethyl acetate, Ritodrine hydrochloride monohydrate for which the main x-ray diffraction peaks, the main and characteristic bands of the IR spectrum and the main and characteristic bands of the Raman spectrum, are shown.

The x-ray powder diffractogram (XRPD) was obtained by using a CuKα1 radiation. The diffractogram is measured in reflection modality in the range of 5-40° 2θ.

The IR spectrum was acquired in ATR modality (Attenuated Total Reflection) and it is measured in $cm^{-1}$.

The Raman spectrum was acquired by using a laser source of 400 mW operating at 785 nm and it is measured in $cm^{-1}$.

DETAILED DESCRIPTION

It has surprisingly been found that Ritodrine hydrochloride exists in two polymorphic forms, Form I and Form II, having very distinct chemical-physical properties. Ritodrine hydrochloride Form I is particularly advantageous with respect to Form II since it is non-hygroscopic. In virtue of this non-hygroscopicity, the chemical-physical properties of Ritodrine hydrochloride Form I can be controlled more easily. All of this is fundamentally important when Ritodrine hydrochloride is formulated.

Vice versa, Ritodrine hydrochloride Form II is hygroscopic. As it is well known in the pharmaceutical industry, the formulation of hygroscopic active ingredients foresees the use of rooms with controlled humidity during the storage and the formulation itself. Moreover, the formulated product must be packaged in a suitable manner so as to avoid problems of stability due to humidity. These problems are avoided when non-hygroscopic Ritodrine hydrochloride Form I is used.

Ritodrine hydrochloride Form I is characterised in that it is non-hygroscopic and stable in its water content as measured through Karl Fischer titration. It has surprisingly been found that Ritodrine hydrochloride Form I does not absorb water even when it is exposed to a relative humidity of 75%.

In the present application, by the term "non-hygroscopic" we mean that Ritodrine hydrochloride Form I absorbs less than 1% of water, like for example less than 0.5%, when it is exposed to an environment with 75% relative humidity.

Vice versa, Ritodrine hydrochloride Form II absorbs water even when it is not exposed directly to a humid environment but in normal controlled storing conditions like those foreseen for active ingredients.

In particular Ritodrine hydrochloride Form I claimed in the present invention is a crystalline solid characterised as follows:

TABLE 1

| XRPD 2θ(°) | IR $cm^{-1}$ | RAMAN $cm^{-1}$ |
| --- | --- | --- |
| 4.87 | 3380 | 3058 |
| 9.24 | 3012 | 3015 |
| 12.52 | 2854 | 2982 |
| 14.15 | 2827 | 2944 |
| 15.17 | 1612 | 2863 |
| 15.71 | 1595 | 1615 |
| 16.49 | 1514 | 1600 |
| 18.06 | 1443 | 1596 |
| 18.51 | 1402 | 1449 |
| 19.20 | 1388 | 1364 |
| 19.67 | 1354 | 1339 |
| 20.41 | 1342 | 1320 |
| 21.64 | 1326 | 1291 |
| 23.04 | 1291 | 1265 |
| 24.08 | 1261 | 1205 |
| 24.94 | 1203 | 1173 |
| 25.71 | 1172 | 1129 |
| 26.12 | 1128 | 1114 |
| 26.48 | 1115 | 1095 |
| 27.18 | 1098 | 1077 |
| 29.48 | 1076 | 1048 |
| 33.22 | 1048 | 1030 |
| 33.55 | 1031 | 1017 |
| 35.01 | 1015 | 993 |
| 35.32 | 992 | 969 |
|  | 969 | 922 |

TABLE 1-continued

| XRPD 2θ(°) | IR cm$^{-1}$ | RAMAN cm$^{-1}$ |
|---|---|---|
|  | 874 | 848 |
|  | 856 | 824 |
|  | 832 | 713 |
|  | 809 | 668 |
|  | 790 | 641 |
|  | 763 | 598 |
|  | 718 | 481 |
|  | 667 | 406 |
|  |  | 390 |
|  |  | 341 |

Ritodrine hydrochloride Form II is a crystalline solid characterised as follows:

TABLE 2

| XRPD 2θ(°) | IR cm$^{-1}$ | RAMAN cm$^{-1}$ |
|---|---|---|
| 9.35 | 3411 | 3057 |
| 12.52 | 3270 | 3016 |
| 14.06 | 3008 | 2946 |
| 15.14 | 2843 | 2911 |
| 15.76 | 2440 | 2879 |
| 16.31 | 1889 | 2864 |
| 17.55 | 1614 | 1616 |
| 18.74 | 1594 | 1602 |
| 19.02 | 1577 | 1594 |
| 19.69 | 1516 | 1448 |
| 20.42 | 1446 | 1419 |
| 20.64 | 1393 | 1321 |
| 21.46 | 1358 | 1290 |
| 22.36 | 1263 | 1265 |
| 23.88 | 1222 | 1208 |
| 24.94 | 1173 | 1139 |
| 26.97 | 1138 | 1073 |
| 28.25 | 1116 | 1046 |
| 31.81 | 1093 | 1014 |
| 32.53 | 1073 | 992 |
| 34.14 | 1046 | 926 |
| 37.97 | 1013 | 879 |
|  | 993 | 848 |
|  | 879 | 825 |
|  | 834 | 718 |
|  | 814 | 642 |
|  | 792 | 472 |
|  | 777 | 449 |
|  | 717 | 394 |
|  | 661 | 362 |
|  |  | 351 |
|  |  | 243 |

Ritodrine hydrochloride Form I can be obtained according to the following methods:
(i) treating Ritodrine hydrochloride in alcoholic solvent with one or more organic solvents so as to obtain a solution and subsequent precipitation of Ritodrine hydrochloride Form I;
or
(ii) transforming Ritodrine hydrochloride solvate or monohydrate or Form II, by suspension in organic solvents, and the subsequent separation of Ritodrine hydrochloride Form I; or
(iii) transforming Ritodrine hydrochloride solvate or monohydrate or Form II, by drying so as to obtain Ritodrine hydrochloride Form I.

In another embodiment of the present invention Ritodrine hydrochloride is obtained according to a method that comprises:
(a) the reaction of 4-(2-bromopropionyl)phenyl methanesulfonate with benzyl-[2-(4-benzyloxyphenyl)-ethyl]-amine to obtain 4-(2-{benzyl-[2-(4-benzyloxy-phenyl)-ethyl]-amino}-propionyl)-phenyl methanesulfonate (B).
(b) the hydrolysis of the product obtained in (a) in the corresponding deprotected form 2-{Benzyl-[2-(4-benzyloxyphenyl)-ethyl]-amino}-1-(4-hydroxy-phenyl)-propan-1-one of formula (C).
(c) the salification of 2-{Benzyl-[2-(4-benzyloxyphenyl)-ethyl]-amino}-1-(4-hydroxy-phenyl)-propan-1-one (C).
(d) the catalytic hydrogenation of 2-{Benzyl-[2-(4-benzyloxyphenyl)-ethyl]-amino}-1-(4-hydroxy-phenyl)-propan-1-one hydrochloride of formula (D) and subsequent concentration, following the separation of the catalyst, through low pressure distillation, so as to obtain Ritodrine hydrochloride (A).

In step (a) 4-(2-bromopropionyl)phenyl methanesulfonate is obtained through bromination of 4-propionyl-phenyl methanesulfonate with bromine. 4-(2-bromopropionyl)phenyl methanesulfonate is subsequently made to react with benzyl-[2-(4-benzyloxyphenyl)-ethyl]-amino in base presence to obtain the methane sulfonic ester 2-{Benzyl-[2-(4-benzyloxyphenyl)-ethyl]-amino}-1-(4-oxy-phenyl)-propan-1-one (B).

In one embodiment, the hydrolysis of the methane sulfonic ester of 2-{Benzyl-[2-(4-benzyloxyphenyl)-ethyl]-amino}-1-(4-oxy-phenyl)-propan-1-one (B) in step (b) is carried out by means of a base that can be, as an example and not for limiting purposes, a hydroxide of alkaline and/or alkaline earth metals, typically potassium hydroxide or sodium hydroxide in a solvent formed by mixtures of acetone-water, methyl ethyl ketone-water or mixtures thereof. The compound (C) obtained is thus isolated through crystallization by acetone, methyl ethyl ketone, mixtures of acetone-water, methyl ethyl ketone-water or mixtures thereof.

In step (c) 2-{Benzyl-[2-(4-benzyloxyphenyl)-ethyl]-amino}-1-(4-hydroxy-phenyl)-propan-1-one (C) is salified with a suitable acid. In one embodiment, the compound (C) is transformed into its corresponding hydrochloride salt (D) by using hydrochloric acid, gaseous or in solution, in a solvent that is selected, as an example and not for limiting purposes, amongst toluene, ethanol, methanol, water, acetone, methyl ethyl ketone, ethyl acetate or mixtures thereof.

Alternatively, a direct conversion of 2-{Benzyl-[2-(4-benzyloxyphenyl)-ethyl]-amino}-1-(4-oxy-phenyl)-propan-1-one methanesulfonate (B) in the salified form 2-{Benzyl-[2-(4-benzyloxyphenyl)-ethyl]-amino}-1-(4-hydroxy-phenyl)-propan-1-one (D) is carried out, without isolation of the free base (C).

In step (d) through treatment with hydrogen in presence of a catalyst, 2-{Benzyl-[2-(4-benzyloxyphenyl)-ethyl]-amino}-1-(4-hydroxy-phenyl)-propan-1-one hydrochloride (D) is converted into the corresponding compound 4-((1RS,2SR)-1-hydroxy-2-{[2-(4-hydroxyphenyl)ethyl]amino}propyl)phenol hydrochloride (Ritodrine hydrochloride) (A). In one embodiment, the catalytic hydrogenation of (D) occurs by using a catalyst made up of a palladium on carbon (Pd/C) in an organic solvent, preferably in alcohol or in alcohol mixed with water. As an example and not for limiting purposes, the alcohol is selected amongst methanol or ethanol or mixtures thereof.

The hydrogenation reaction is carried out in a hydrogen atmosphere according to what is known by a man skilled in the art and in particular with a pressure that is preferably comprised between 2 and 12 bar and at temperatures comprised between 20° C. and 45° C. In such conditions, and differently from what is shown in EP0492719, the reaction is very selective and provides an erythro/threo mixture of about 98:2.

The solution of Ritodrine hydrochloride obtained from the hydrogenation reaction, following filtration of the catalyst, is concentrated through low pressure distillation.

Ritodrine hydrochloride in alcoholic solvent obtained from the hydrogenation reaction is subsequently diluted with ethers or aliphatic hydrocarbons such as, as an example and not for limiting purposes, methyl-tert-butyl ether, heptane or mixtures thereof or methyl ethyl ketone until the precipitation of Ritodrine hydrochloride is obtained. The solid is isolated through filtration.

The humid solid thus obtained has the desired crystalline form, Form I. In a further embodiment, Ritodrine hydrochloride in alcoholic solvent used to obtain Form I, as described above, is obtained by mixing solid Ritodrine hydrochloride with an alcoholic solvent.

In another aspect of the present invention, the solution of Ritodrine hydrochloride obtained by the hydrogenation reaction, after filtration of the catalyst and subsequent concentration through low pressure distillation, is precipitated as a solvated form through treatment with suitable organic solvents.

In a further embodiment, Ritodrine hydrochloride in alcoholic solvent, used to obtain the solvate, is obtained by mixing solid Ritodrine hydrochloride with alcoholic solvent and subsequent precipitation through treatment with suitable organic solvents.

Suitable organic solvents used for the precipitation of Ritodrine hydrochloride solvate comprise, as an example and not for limiting purposes, acetone, ethyl acetate or mixtures thereof. The precipitation of Ritodrine hydrochloride can be possibly primed. The isolation of Ritodrine hydrochloride as a solved form is very advantageous since it provides Ritodrine hydrochloride with high chemical purity. The product obtained is Ritodrine hydrochloride solvate with a chemical purity that is greater than 98%, typically greater than 99% or greater than 99.8%.

As an example and not for limiting purposes, one example of Ritodrine hydrochloride solvate is the solvate with acetone, which is characterised as follows:

TABLE 3

| XRPD 2θ (°) | IR cm$^{-1}$ | RAMAN cm$^{-1}$ |
| --- | --- | --- |
| 3.75 | 3262 | 3061 |
| 7.49 | 3004 | 3018 |
| 11.50 | 2952 | 3004 |
| 14.24 | 2820 | 2954 |
| 14.98 | 2431 | 2856 |
| 16.29 | 1698 | 1692 |
| 17.35 | 1615 | 1618 |
| 19.02 | 1593 | 1600 |
| 20.32 | 1564 | 1549 |
| 21.06 | 1548 | 1478 |
| 21.65 | 1515 | 1446 |
| 22.42 | 1454 | 1424 |
| 23.23 | 1390 | 1305 |
| 24.06 | 1367 | 1290 |
| 24.87 | 1310 | 1266 |
| 25.30 | 1290 | 1213 |
| 25.80 | 1263 | 1196 |
| 26.38 | 1236 | 1168 |
| 26.93 | 1217 | 1153 |
| 32.15 | 1191 | 1118 |
| 35.48 | 1169 | 1075 |
|  | 1151 | 1052 |
|  | 1118 | 1020 |
|  | 1097 | 993 |
|  | 1075 | 928 |
|  | 1053 | 885 |
|  | 1020 | 848 |

TABLE 3-continued

| XRPD 2θ (°) | IR cm$^{-1}$ | RAMAN cm$^{-1}$ |
| --- | --- | --- |
|  | 993 | 815 |
|  | 959 | 798 |
|  | 936 | 765 |
|  | 908 | 717 |
|  | 885 | 658 |
|  | 872 | 642 |
|  | 843 | 580 |
|  | 829 | 546 |
|  | 815 | 343 |
|  | 789 |  |
|  | 765 |  |
|  | 718 |  |
|  | 660 |  |

As an example and not for limiting purposes, a further example of Ritodrine hydrochloride solvate is the solvate with ethyl acetate, which is characterised as follows:

TABLE 4

| XRPD 2θ (°) | IR cm$^{-1}$ | RAMAN cm$^{-1}$ |
| --- | --- | --- |
| 7.37 | 3338 | 3062 |
| 7.87 | 3101 | 3017 |
| 9.01 | 2979 | 2982 |
| 14.73 | 2799 | 2944 |
| 15.75 | 2465 | 2873 |
| 16.43 | 1742 | 1735 |
| 16.62 | 1730 | 1617 |
| 17.09 | 1615 | 1602 |
| 17.85 | 1595 | 1546 |
| 18.67 | 1579 | 1449 |
| 19.39 | 1546 | 1411 |
| 19.69 | 1514 | 1285 |
| 20.60 | 1441 | 1265 |
| 20.88 | 1410 | 1207 |
| 21.91 | 1392 | 1185 |
| 22.27 | 1372 | 1174 |
| 22.73 | 1342 | 1152 |
| 23.66 | 1264 | 1115 |
| 24.19 | 1220 | 1107 |
| 25.19 | 1171 | 1072 |
| 26.18 | 1150 | 1044 |
| 27.12 | 1115 | 1012 |
| 30.70 | 1090 | 928 |
|  | 1070 | 884 |
|  | 1043 | 848 |
|  | 1010 | 823 |
|  | 991 | 776 |
|  | 938 | 718 |
|  | 882 | 654 |
|  | 847 | 642 |
|  | 829 | 635 |
|  | 791 | 473 |
|  | 767 | 447 |
|  | 714 | 382 |
|  | 656 | 354 |
|  |  | 205 |

In another aspect of the present invention, the solution of Ritodrine hydrochloride obtained by the hydrogenation reaction, after filtration of the catalyst and subsequent concentration through low pressure distillation, is precipitated as a monohydrate through treatment with an aqueous solution. The precipitation of Ritodrine hydrochloride can be possibly primed. The mixture thus obtained is left to crystallise keeping it under stirring at a temperature comprised between 15° C. and 30° C., preferably at 20° C. for a time of from 4 to 48 hours, preferably from 10 to 24 hours.

In a further embodiment, Ritodrine hydrochloride monohydrate is obtained by mixing solid Ritodrine hydrochloride and an aqueous solution.

The compound obtained in such conditions is Ritodrine hydrochloride monohydrate with a chemical purity that is greater than 98%, typically greater than 99% or greater than 99.8%. Ritodrine hydrochloride monohydrate is characterised as follows:

TABLE 5

| XRPD 2θ(°) | IR cm$^{-1}$ | RAMAN cm$^{-1}$ |
|---|---|---|
| 3.77 | 3479 | 3093 |
| 7.51 | 3407 | 3060 |
| 11.50 | 3187 | 3015 |
| 14.24 | 3052 | 2989 |
| 15.00 | 2977 | 2962 |
| 16.27 | 2825 | 2947 |
| 17.37 | 2685 | 2915 |
| 19.02 | 2602 | 2887 |
| 20.33 | 2448 | 2865 |
| 20.75 | 1614 | 1616 |
| 21.08 | 1601 | 1602 |
| 21.66 | 1568 | 1577 |
| 22.35 | 1515 | 1476 |
| 23.26 | 1453 | 1446 |
| 23.85 | 1373 | 1427 |
| 24.08 | 1353 | 1389 |
| 24.87 | 1314 | 1368 |
| 25.31 | 1294 | 1312 |
| 25.78 | 1278 | 1295 |
| 26.37 | 1230 | 1279 |
| 26.92 | 1175 | 1258 |
| 28.67 | 1127 | 1216 |
| | 1099 | 1205 |
| | 1071 | 1189 |
| | 1044 | 1132 |
| | 1010 | 1109 |
| | 985 | 1072 |
| | 964 | 1041 |
| | 903 | 1015 |
| | 882 | 987 |
| | 851 | 943 |
| | 826 | 903 |
| | 809 | 883 |
| | 785 | 855 |
| | 753 | 831 |
| | 716 | 827 |
| | 701 | 809 |
| | 655 | 789 |
| | | 718 |
| | | 639 |
| | | 570 |
| | | 524 |
| | | 450 |
| | | 420 |
| | | 390 |
| | | 357 |

The water content of Ritodrine hydrochloride monohydrate determined through Karl Fischer titration is 5.3% (weight/weight) and is congruous with the presence of one molecule of water in the crystal lattice.

It has surprisingly been observed that Ritodrine hydrochloride Form I can be obtained even from other crystalline forms of Ritodrine hydrochloride like the solvate, the monohydrate and Form II. In one embodiment, the transformation occurs wet, by suspension in organic solvents, and the subsequent separation of Ritodrine hydrochloride Form I. In a further embodiment of this invention, the suspension of Ritodrine hydrochloride solvate, monohydrate or From II, is carried out in ethers or aliphatic hydrocarbons such as methyl-tert-butyl ether, or heptane, or methyl ethyl ketone or mixtures thereof.

The suspension in such solvents is carried out through stirring at a temperature greater than 0° C., preferably between 20° C. and the boiling point of the solvent and even more preferably at a temperature comprised between 30° C. and 50° C. for at least 1 hour.

The transformation of Ritodrine hydrochloride in the desired form, Form I, can be monitored by using suitable methods that are known by a man skilled in the art.

In another aspect of the present invention, the transformation occurs dry. It has surprisingly been observed that Ritodrine hydrochloride solvate or monohydrate or Form II, is transformed into Ritodrine hydrochloride Form I through a drying process. It has surprisingly been discovered that such transformations occur at specific temperatures and over specific amounts of time. When these conditions are not scrupulously applied, Ritodrine hydrochloride is, instead, obtained as Form II, or as a mixture of Form I and Form II. It is obvious that the presence of Form II in the active ingredient is not desired. The transformation in dry conditions of Ritodrine hydrochloride Form I occurs by acting at a temperature of at least 60° C. and preferably at temperatures of between 75° C. and 85° C. for at least 1 hour.

The transformation of Ritodrine hydrochloride into the desired form, Form I, can be monitored by using suitable methods that are known by a man skilled in the art. The transformation in dry conditions of Ritodrine hydrochloride Form I can occur even at temperatures that are greater than 85° C. but with partial decomposition of the compound with the formation of by-products such as tyramine causing there to be reduced chemical purity of the active ingredient.

In another aspect of the present invention, the chemical purity of Ritodrine hydrochloride can be increased even through a process of
a') recrystallization with complete dissolution; or
b') resuspension in organic solvents without reaching complete dissolution; followed by the separation of the solid which is Ritodrine hydrochloride.

In the examples that follow, as an example and not for limiting purposes, the application of the present invention is illustrated.

EXPERIMENTAL PART

X-ray powder diffractograms (XRPD) were obtained by using a CuKα1 radiation. The diffractograms were measured in reflection modality in the range 5-40° 2θ.

The IR spectrums were acquired in ATR (Attenuated Total Reflection) modality and measured in cm$^{-1}$.

The Raman spectrums were acquired by using a laser source of 400 mW operating at 785 nm and measured in cm$^{-1}$.

The water content was determined through Karl Fischer (KF) titration.

Example 1

Preparation of 4-(2-{benzyl-[2-(4-benzyloxyphenyl)-ethyl]-amino}-propionyl)phenyl methanesulfonate (B)

100 g of 4-propionyl-phenyl methanesulfonate and 360 ml of dichloromethane were loaded into a 2 liter reactor. The solution obtained was cooled to 0° C. and, at such a temperature, 3 g of solution with 33% of Hbr in acetic acid and subsequently 23 ml of Br$_2$ (71.6 g) were added. Once these were added, the solution obtained was left under stirring for 1 hour at a temperature of around 0° C.

200 ml of H$_2$O were added to the solution, then the mass was heated to 20° C. and kept at such a temperature for 30 minutes.

Once the stirring had stopped the two phases were separated and the organic phase was reloaded on the reactor and 260 ml of ethanol were added to it.

The solution obtained was heated to around 80° C. progressively distilling the dichloromethane, then cooled to 40° C. and diluted with 1780 ml of ethanol.

133.2 g of benzyl-[2-(4-benzyloxyphenyl)-ethyl]-amine and subsequently 104 ml of triethylamine were added to it under stirring. The mass was heated to reflux and was kept at reflux for about 18 hours, then it was gradually cooled down to room temperature, obtaining a suspension that was then filtered.

The crystalline solid obtained was vacuum dried at 60° C. for 10 hours.

195 g of 4-(2-{benzyl-[2-(4-benzyloxyphenyl)-ethyl]-amino}-propionyl)phenyl methanesulfonate (B) were obtained.

Molar yield 82%, purity 97.5% HPLC (A %).

Example 2

4-(2-{benzyl-[2-(4-benzyloxyphenyl)-ethyl]-amino}-propionyl)phenyl methanesulfonate (B)

100 g of 4-(2-bromopropionyl)-phenyl methanesulfonate and 1750 ml of ethanol were loaded into a 3 liter reactor.

103 g of benzyl-[2-(4-benzyloxyphenyl)-ethyl]-amino and after 77 ml of triethylamine were added to it under stirring. The mass was heated to reflux and kept at reflux for about 18 hours, then it was gradually cooled down to room temperature, obtaining a suspension that was then filtered.

The crystalline solid obtained was vacuum dried at 60° C. for 10 hours.

148.96 g of 4-(2{benzyl-[2-(4-benzyloxy-phenyl)-ethyl]-amino}-propionyl)-phenyl methanesulfonate (B) were obtained.

Molar yield 84%, purity 98.4% HPLC (A %).

Example 3

Preparation of 2-{Benzyl-[2-(4-benzyloxyphenyl)-ethyl]-amino}-1-(4-hydroxy-phenyl)-propan-1-one (C)

50 g of 4-(2-{benzyl-[2-(4-benzyloxyphenyl)-ethyl]-amino}-propionyl)phenyl methanesulfonate (B), 100 ml of water, 355 ml of acetone and 18.4 g of potassium hydroxide are introduced into a one liter glass reactor at room temperature. The mixture is heated to reflux temperature (about 59° C.) and kept at such a temperature for two hours. Subsequently, the mixture is cooled down to 45-50° C. and 30% hydrochloric acid is added until a pH of around 7 is obtained. The lower phase is separated and the organic phase is diluted with 100 ml of water. A suspension is obtained that is cooled down to 0° C. The solid is isolated through filtration and washed and then vacuum dried at 40° C. 41.4 g of 2-{Benzyl-[2-(4-benzyloxy-phenyl)-ethyl]-amino}-1-(4-hydroxy-phenyl)-propan-1-one (C) as a white solid, are obtained.

Molar yield 96%, chemical purity 99.63% HPLC (A %).

Example 4

Preparation of 2-{Benzyl-[2-(4-benzyloxyphenyl)-ethyl]-amino}-1-(4-hydroxy-phenyl)-propan-1-one hydrochloride (D)

20 g of 2-{Benzyl-[2-(4-benzyloxyphenyl)-ethyl]-amino}-1-(4-hydroxy-phenyl)-propan-1-one and 100 ml of methyl ethyl ketone are introduced into a 250 ml reactor. At 20° C., 9 g of a solution with 19% by weight of HCl in 2-butanone are added. Once the precipitation of the solid has occurred, it is heated to 50° C. and it is diluted with 40 ml of methyl ethyl ketone. It is kept under stirring for an hour and then it is cooled down again to 20° C. The solid is filtered and is washed with 80 ml of methyl ethyl ketone. After vacuum drying at 40° C., 20.6 g of 2-{Benzyl-[2-(4-benzyloxyphenyl)-ethyl]-amino}-1-(4-hydroxy-phenyl)-propan-1-one hydrochloride as a white solid, are obtained.

Molar yield 95%, chemical purity: 99.76% HPLC (A %).

Example 5

Preparation of 2-{Benzyl-[2-(4-benzyloxyphenyl)-ethyl]-amino}-1-(4-hydroxy-phenyl)-propan-1-one hydrochloride (D)

400 g of 2-{Benzyl-[2-(4-benzyloxyphenyl)-ethyl]-amino}-1-(4-hydroxy-phenyl)-propan-1-one and 2000 ml of acetone are loaded into a one liter glass reactor, at room temperature. Keeping the temperature at 20° C., 34.8 g of gaseous hydrochloric acid is injected. Once the acid has been added it is primed with 2-{Benzyl-[2-(4-benzyloxyphenyl)-ethyl]-amino}-1-(4-hydroxy-phenyl)-propan-1-one hydrochloride, obtaining the precipitation of the product. The suspension is kept under stirring at 20° C. over night. The product is finally isolated through filtration, washed with 200 ml of acetone and vacuum dried at 40° C. 413 g of 2-{Benzyl-[2-(4-benzyloxyphenyl)-ethyl]-amino}-1-(4-hydroxy-phenyl)-propan-1-one hydrochloride as a white solid, are obtained.

Molar yield 95%, chemical purity 99.84% HPLC (A %)

Example 6

Preparation of 2-{Benzyl-[2-(4-benzyloxyphenyl)-ethyl]-amino}-1-(4-hydroxy-phenyl)-propan-1-one hydrochloride (D)

A 500 ml reactor was loaded with 20 g of 2-{Benzyl-[2-(4-benzyloxyphenyl)-ethyl]-amino}-1-(4-hydroxy-phenyl)-propan-1-one, 200 ml of toluene and 10 ml of ethanol. The suspension thus obtained was brought to the temperature of 50° C. and at such a temperature, under stirring, 4 ml of 37% HCl were added, observing the complete dissolution of the suspended solid.

The solution was then cooled down first to 32° C. and then to 0° C. The solid obtained through crystallization was filtered, washed with 15 ml of isopropanol and vacuum dried at 55° C.

21 g of 2-{Benzyl-[2-(4-benzyloxyphenyl)-ethyl]-amino}-1-(4-hydroxy-phenyl)-propan-1-one hydrochloride (D) were obtained as a white solid.

Molar yield 97%, purity 99.66% HPLC (A %).

Example 7

Hydrogenation of 2-{Benzyl-[2-(4-benzyloxyphenyl)-ethyl]-amino}-1-(4-hydroxy-phenyl)-propan-1-one hydrochloride (D)

A 5 liter steel autoclave is loaded with 130 g of 2-{Benzyl-[2-(4-benzyloxyphenyl)-ethyl]-amino}-1-(4-hydroxy-phenyl)-propan-1-one hydrochloride (D), 481 ml of methanol and 4.6 g of 5% palladium on carbon.

The mixture is heated to 30° C. and keeping the pressure at 6 bar hydrogen is injected until there is zero absorption. The mixture is filtered to remove the catalyst obtaining 504 g of alcoholic solution of Ritodrine hydrochloride.

Chemical purity (area, HPLC): Ritodrine hydrochloride 98.1%; threo isomers 1.3%.

Example 8

Hydrogenation of 2-{Benzyl-[2-(4-benzyloxyphenyl)-ethyl]-amino}-1-(4-hydroxy-phenyl)-propan-1-one hydrochloride (D)

A 5 liter steel autoclave is loaded with 716 g of 2-{Benzyl-[2-(4-benzyloxyphenyl)-ethyl]-amino}-1-(4-hydroxy-phenyl)-propan-1-one hydrochloride (D), 2650 ml of absolute ethanol and 107.7 g of 5% palladium on carbon 60% humid. The mixture is heated to 40° C. and keeping the pressure at 6 bar, hydrogen is injected until there is zero absorption. The mixture is filtered to remove the catalyst obtaining 2778 g of alcoholic solution of Ritodrine hydrochloride. Chemical purity (area, HPLC): Ritodrine hydrochloride 98.1%; threo isomers 1.2%.

Example 9

4-((1RS,2SR)-1-hydroxy-2-{[2-(4-hydroxyphenyl)ethyl]amino}propyl)phenol hydrochloride (Ritodrine hydrochloride) Form I.

A methanolic solution of ritodrine hydrochloride obtained as described in Example 8 was concentrated as a residue and was diluted with 89 ml of methanol.
The solution thus obtained is treated with 1180 ml of methyl-tert-butyl ether and heated to 37° C. obtaining a suspension. It is stirred for 11 hours and then cooled down to 20° C., it is filtered and the solid is washed with methyl-tert-butyl ether. It is vacuum dried at 40° C. obtaining 76.8 g of Ritodrine hydrochloride. The X-ray diffraction pattern corresponds to that of Ritodrine hydrochloride Form I shown in table 1.

Example 10

4-((1RS,2SR)-1-hydroxy-2-{[2-(4-hydroxyphenyl)ethyl]amino}propyl)phenol hydrochloride (Ritodrine hydrochloride) solvated with acetone.

A methanolic solution of ritodrine hydrochloride obtained as described in Example 8 was concentrated as a residue through low pressure distillation.
The residue is diluted with 10 ml of methanol and 650 ml of acetone. The mixture is brought to 37° C. and is kept under stirring at 37° C. for 11 hours. It is cooled down to room temperature and the product is isolated through filtration. It is washed with 200 ml of acetone and 102 g of Ritodrine hydrochloride are obtained. Chemical purity: 99.84% HPLC (A %). The X-ray diffraction pattern corresponds to that of Ritodrine hydrochloride solvated with acetone shown in table 3.

Example 11

4-((1RS,2SR)-1-hydroxy-2-{[2-(4-hydroxyphenyl)ethyl]amino}propyl)phenol hydrochloride (Ritodrine hydrochloride) solvated with ethyl acetate 100 g of an ethanolic solution of Ritodrine hydrochloride obtained according to the method described in example 8, containing about 15 g of Ritodrine hydrochloride, are concentrated by vacuum distilling 50 g of solvent. The solution thus obtained is cooled down to 0° C. 200 ml of ethyl acetate are dripped obtaining the precipitation of the product. The suspension is kept under stirring over night at 0° C. The solid is filtered. 14.5 g of Ritodrine hydrochloride are obtained.
Chemical purity: 99.25% HPLC (A %). The X-ray diffraction pattern corresponds to that of Ritodrine hydrochloride solvated with ethyl acetate shown in table 4.

Example 12

4-((1RS,2SR)-1-hydroxy-2-{[2-(4-hydroxyphenyl)ethyl]amino}propyl)phenol hydrochloride (Ritodrine hydrochloride)monohydrate 25 g of Ritodrine hydrochloride is suspended in 50 ml of water and is kept stirred at 20° C. for 20 hours. It is then cooled down to 0° C. in about an hour and it is kept at 0° C. for 3 hours.
The solid is filtered and is vacuum dried at 50° C. for 24 hours. 21 g of Ritodrine hydrochloride monohydrate are obtained.
The X-ray diffraction pattern is the same as that of Ritodrine hydrochloride monohydrate shown in table 5.

Example 13

Transformation of Ritodrine Hydrochloride Solvated with Acetone into Ritodrine Hydrochloride Form I 20 g of Ritodrine hydrochloride solvated with acetone obtained as described in example 10 are suspended in 40 ml of methyl-tert-butyl ether. The suspension is kept stirred at 50° C.-55° C. for 3 hours and is then cooled down to 20° C. It is filtered and washed with methyl-tert-butyl ether and is vacuum dried at 50° C.
13.3 g of Ritodrine hydrochloride Form I are obtained.

Example 14

Transformation of Ritodrine Hydrochloride Solvated with Acetone into Ritodrine Hydrochloride Form I 20 g of Ritodrine hydrochloride solvated with acetone obtained as described in example 10 are suspended in 100 ml of heptane. The suspension is heated to reflux temperature for 1-1.5 hours and is then cooled down to 20° C. The solid is filtered and is vacuum dried at 50° C. 13.8 g of Ritodrine hydrochloride Form I are obtained.

Example 15

Transformation of Ritodrine Hydrochloride Monohydrate into Ritodrine Hydrochloride Form I Ritodrine hydrochloride monohydrate is placed to vacuum dry in an oven at a temperature of 80° C. for 12 hours. Ritodrine hydrochloride Form I is obtained.

Example 16

Transformation of Ritodrine Hydrochloride Solvated with Ethyl Acetate into Ritodrine Hydrochloride Form I Ritodrine hydrochloride solvated with ethyl acetate is placed to vacuum dry in an oven at a temperature of 80° C. for 26 hours. Ritodrine hydrochloride Form I is obtained.

Example 17

Preparation of Ritodrine Hydrochloride Form II

Ritodrine hydrochloride solvated with acetone is placed to vacuum dry in an oven at a temperature of 40° C. for 22 hours. Ritodrine hydrochloride Form II is obtained. The X-ray diffraction pattern corresponds to that of Ritodrine hydrochloride Form II shown in table 2.

Example 18

Transformation of Ritodrine Hydrochloride Form II into Ritodrine Hydrochloride Form I Ritodrine hydrochloride Form II is placed to vacuum dry in an oven at a temperature of 80° C. for 17 hours. Ritodrine hydrochloride Form I is obtained.

Example 19

Recrystallization of Ritodrine Hydrochloride 100 g of Ritodrine hydrochloride are suspended at room temperature in 300 ml of methyl ethyl ketone. 80 ml of methanol are added obtaining a solution that is subsequently heated to 37° C. and diluted with 700 ml of methyl ethyl ketone. The precipitation is started by adding a primer. The suspension is kept at 37° C. for 4 hours and is then left to cool down to room temperature. It is filtered and washed with 200 ml of methyl ethyl ketone. The solid is vacuum dried at 60° C. obtaining 60 g of Ritodrine hydrochloride Form I. Chemical purity 99.9% HPLC (A %).

Example 20

Stability of Ritodrine Hydrochloride Form I

Ritodrine hydrochloride Form I is kept at 40° C. and a relative humidity of 75% for 24 hours. The water content measured through Karl Fischer titration is 0.5% (weight/weight).

Example 21

Stability of Ritodrine Hydrochloride Form II

Ritodrine hydrochloride Form II is placed in a double polyethylene bag with a desiccant (silica gel) kept in standard conditions for storing active ingredients. After some months the water content of such Ritodrine hydrochloride measured through Karl Fischer titration is 2.2% (weight/weight).

The invention claimed is:

1. A method for preparing ritodrine hydrochloride comprising:
    (a) reacting of 4-(2-bromopropionyl)phenyl methanesulfonate with benzyl-[2-(4-benzyloxyphenyl)-ethyl]-amine to obtain 4-(2{benzyl-[2-(4-benzyloxy-phenyl)-ethyl]-amino}-propionyl)-phenyl methanesulfonate;
    (b) hydrolyzing of 4-(2-{benzyl-[2-(4-benzyloxyphenyl)-ethyl]-amino}-propionyl)-phenyl methanesulfonate to obtain 2-{Benzyl-[2-(4-benzyloxyphenyl)-ethyl]-amino}-1-(4-hydroxy-phenyl)-propan-1-one;
    (c) salificating of 2-{Benzyl-[2-(4-benzyloxyphenyl)-ethyl]amino}-1-(4-hydroxy -phenyl-propan-1-one; and
    (d) catalytically hydrogenating of 2-{Benzyl-[2-(4-benzyloxyphenyl)-ethyl]-amino}-1-(4-hydroxy-phenyl)-propan-1-one hydrochloride to obtain Ritodrine hydrochloride as an erythro/threo mixture about of 98:2.

2. The method of claim 1, wherein hydrolyzing in (b) is performed using a base comprising an alkaline metal and/or earth alkaline hydroxide, potassium hydroxide or sodium hydroxide in a solvent made of mixtures of acetone-water, methyl ethyl ketone-water or mixtures thereof.

3. The method of claim 2, wherein 2-{Benzyl-[2 (4-benzyloxyphenyl)-ethyl]-amino}-1-(4-ydroxyl-phenyl)-propan-1-one is isolated by crystallisation from acetone, methyl ethyl ketone, mixtures of acetone-water, methyl ethyl ketone-water or mixtures thereof.

4. The method of claim 1, wherein the salificating step uses hydrochloric acid, gaseous or in solution, in an organic solvent, wherein the organic solvent comprises toluene or ethanol or methanol or water or acetone or methyl ethyl ketone or ethyl acetate or mixtures thereof.

5. The method of claim 1, wherein 2-{Benzyl-[2-(4-benzyloxyphenyl)-ethyl]-amino}-1-(4-oxy-phenyl)-propan-1-one methanesulfonate is directly transformed into 2-{Benzyl-[2-(4-benzyloxyphenyl)-ethyl]-amino}-1-(4-hydroxy-phenyl) -propan-1-one hydrochloride salt.

6. The method of claim 1, wherein the catalytically hydrogenating step of 2-{Benzyl-[2-(4-benzyloxyphenyl)-ethyl]-amino}-1-(4-hydroxy -phenyl)-propan-1-one hydro-chloride comprises palladium on carbon (Pd/C) catalyst in an organic solvent, wherein the organic solvent is an alcohol or an alcohol mixed with water, in a hydrogen atmosphere between about 2 and about 12 bars, at temperatures between about 20° C. and about 45° C.

* * * * *